United States Patent [19]
Flaugh et al.

[11] Patent Number: 5,462,962
[45] Date of Patent: Oct. 31, 1995

[54] TETRAHYDROBENZ[C,D]INDOLE SEROTONIN AGONISTS

[75] Inventors: Michael E. Flaugh; Mark M. Foreman, both of Indianapolis, Ind.

[73] Assignee: Eli Lilly and Company, Indianapolis, Ind.

[21] Appl. No.: 992,410

[22] Filed: Dec. 15, 1992

Related U.S. Application Data

[60] Division of Ser. No. 482,811, Feb. 26, 1990, Pat. No. 5,204,340, which is a continuation-in-part of Ser. No. 336,409, Apr. 11, 1989, abandoned.

[51] Int. Cl.$^6$ .......................... A61K 31/40; A61K 31/535
[52] U.S. Cl. .............................................................. 514/411
[58] Field of Search ............................................... 514/411

[56] References Cited

U.S. PATENT DOCUMENTS

| | | | |
|---|---|---|---|
| 4,110,339 | 8/1978 | Bach et al. | 260/326.9 |
| 4,576,959 | 3/1986 | Flaugh | 514/411 |
| 4,640,921 | 2/1987 | Othmer et al. | 514/252 |
| 4,745,126 | 5/1988 | Leander | 514/411 |
| 4,983,622 | 1/1991 | Flaugh | 514/411 |
| 5,021,438 | 6/1991 | Junge et al. | 514/373 |
| 5,204,340 | 4/1993 | Flaugh et al. | 514/210 |
| 5,229,409 | 7/1993 | Flaugh et al. | 514/411 |
| 5,229,410 | 7/1993 | Flaugh et al. | 514/411 |
| 5,302,612 | 4/1994 | Flaugh et al. | 514/411 |

FOREIGN PATENT DOCUMENTS

| | | | |
|---|---|---|---|
| 029581 | 6/1981 | European Pat. Off. | |
| 148440 | 7/1985 | European Pat. Off. | |
| 0153083 | 8/1985 | European Pat. Off. | 514/411 |
| 332968 | 9/1989 | European Pat. Off. | |

OTHER PUBLICATIONS

Kostowski et al., *Pharmacol. Toxicol.*, 71, pp. 24–30 (1992).
Fuller, *Frontiers in Neuroendocrinology*, 13(3), pp. 250–270 (1992).
Flaugh et al., *J. Med. Chem.*, 31, 1746–1753 (1988).
*Tetrahedron Letters* 21, 4061 (1980).
Kornfeld et al., *J.A.C.S.*, 78, 3087 (1956).
Morrison and Boyd, Chapter 22, *Org. Chem.*, 3rd Ed. (1973).
Schoenberg and Heck, *Journal of Organic Chemistry*, 39, 3327 (1974).
Schoenberg, Bartoletti and Heck, *Journal of Organic Chemistry*, 39, 3118 (1974).
T. W. Greene, Chapter 7, *Protective Groups in Org. Synth.* (1981).
J. W. Barton, Chapter 2, *Protective Groups in Org. Chem.* (1981).
Leanna et al., *Tetrahedron Letters* 30, 3935 (1989).
Wong et al., *J. Neural Transmission*, 64, 251 (1985).
*The Merck Manual* Rahway N.J., Merck and Company, 1657–1667 (1987).
Mathes et al., *Pharmacology, Biochem and Behavior* 36, 63–68 (1990).
Glaser et al., *Brain 5–HT$_{1A}$ Receptors*, Chapter 9, 106–119 (1987).
Ahlenius et al., *Brain 5–HT$_{1A}$ Receptors*, Chapter 16, 185–198 (1987).
Othmer et al., *J. Clin. Psychiatry*, 48, 201–203 (1987).

*Primary Examiner*—José G. Dees
*Assistant Examiner*—B. Frazier
*Attorney, Agent, or Firm*—Roger S. Benjamin; Douglas J. Taylor; David E. Boone

[57] ABSTRACT

This invention provides 6-substituted-4-(amino or substituted amino)tetrahydrobenz[c,d]indole serotonin agonists useful in treating a variety of conditions associated with serotonin function.

8 Claims, No Drawings

5,462,962

TETRAHYDROBENZ[C,D]INDOLE SEROTONIN AGONISTS

CROSS REFERENCE TO RELATED APPLICATIONS

This application is a division of application Ser. No. 07/482,811, filed Feb. 26, 1990, now U.S. Pat. No. 5,204,340, which is a continuation in part of application Ser. No. 07/336,409, filed Apr. 11, 1989, now abandoned.

FIELD OF THE INVENTION

This invention relates to the fields of synthetic organic chemistry and pharmaceutical chemistry and involves tetrahydrobenz[cd]indoles which are useful as serotonin agonists.

BACKGROUND OF THE INVENTION

Flaugh in U.S. Pat. No. 4,576,959 (issued 1986) disclosed a family of 6-substituted-4-dialkylamino- 1,3,4,5-tetrahydrobenz[cd]indoles which are described as central serotonin agonists. Leander in U.S. Pat. No. 4,745,126 (1988) disclosed a method for treating anxiety in humans employing a 4-substituted-1,3,4,5-tetrahydrobenz[ cd]indole-6-carboxamide derivative.

A new group of 6-substituted indoles have now been found to be useful in treating conditions requiring enhancement of the serotonin function in the body.

SUMMARY OF THE INVENTION

This invention relates to a compound of the Formula (I)

wherein:

$R^1$ is hydrogen, $C_1$–$C_4$ alkyl, allyl or $$-\overset{O}{\underset{\|}{C}}-R^4;$$

$R^2$ is hydrogen, $C_1$–$C_4$ alkyl or allyl;

$R^3$ is hydrogen, $C_1$–$C_4$ alkoxy, —$NR^5R^6$, or $C_1$–$C_4$ alkylthio;

$R^4$ is hydrogen, methyl, ethyl or vinyl;

$R^5$ and $R^6$ are independently a $C_1$–$C_4$ alkyl, a $C_1$–$C_4$ alkyl substituted with a phenyl group, phenyl, or together form a $C_3$–$C_5$ heterocyclic ring;

X is O or S; or a pharmaceutically acceptable salt thereof.

The invention also provides a pharmaceutical formulation comprising a compound of Formula (I) and a pharmaceutically acceptable carrier, diluent or excipient therefor.

Further embodiments of the invention are methods of treating conditions requiring enhancement of serotonin function in the body as hereinafter described comprising administering to a mammal in need of such treatment a compound of Formula (I).

DETAILED DESCRIPTION OF THE INVENTION

As used herein, the term "$C_1$–$C_4$ alkyl" represents a straight or branched alkyl chain having from one to four carbon atoms. Typical $C_1$–$C_4$ alkyl groups include methyl, ethyl, n-propyl, isopropyl, n-butyl, sec.-butyl and the like.

The term "$C_1$–$C_4$ alkoxy" represents methoxy ($CH_3O$—), ethoxy ($CH_3CH_2O$—), and the like.

The term "$C_1$–$C_4$ alkylthio" represents methylthio ($CH_3S$—) ethylthio ($CH_3CH_2S$—) and the like.

The term "$C_1$–$C_4$ alkyl substituted with a phenyl group" includes phenylmethyl, 1-phenylethyl, and the like.

The term "$C_3$–$C_5$ heterocyclic ring" includes pyrrolidine, piperidine, morpholine and the like.

While all of the compounds of the invention are useful for the purposes taught herein, certain of the present compounds are preferred for such uses. Preferably X is oxygen, $R^1$ and $R^2$ are both $C_1$–$C_4$ alkyl, and especially n-propyl, and $R^3$ is $C_1$–$C_3$ alkoxy, and especially methoxy or ethoxy. Other preferred aspects of the present invention are noted hereinafter.

As pointed out above, this invention includes the pharmaceutically-acceptable salts of the compounds of Formula (I). Since the compounds of this invention are amines, they are basic in nature and accordingly react with any number of inorganic and organic acids to form pharmaceutically acceptable salts such as hydrochloric acid, nitric acid, phosphoric acid, sulfuric acid, hydrobromic acid, hydroiodic acid, phosphorous acid and others, as well as salts derived from non-toxic organic acids such as aliphatic mono and dicarboxylic acids, amino acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, tartrate isobutyrate, caprate, heptanoate, propiolate, oxalate, malonate, succinate, suberate, sebacate, fumarate, maleate, mandelate, butyne-1,4-dioate, hexyne-1,6-dioate, hippurate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, naphthalene-1-sulfonate, naphthalene-2-sulfonate and mesylate.

The compounds of the present invention have an asymmetric center at the carbon atom at the 4-position of the tetrahydrobenz[c,d]indole ring. As such the compounds can exist as either the racemic mixture, or as the individual stereoisomers. All such types of compounds are contemplated by the present invention.

The following list illustrates representative compounds of the present invention:

(±)-4-(dimethylamino)-1,3,4,5-tetrahydrobenz[ c,d]indole-6-carbothioic acid, S-methyl ester (±)-4-(di-n-propylamino)-1,3,4,5-tetrahydrobenz[ c,d]indole-6-carbothioic acid, O-ethyl ester (+)-4-(methylethylamino)-1,3,4,5-tetrahydrobenz[ c,d]indole-6-carbodithioic acid, methyl ester (+)-4-(n-butylamino)-1,3,4,5-tetrahydrobenz[ c,d]indole-6-carboxylic acid, ethyl ester (−)-4-(n-propylamino)-1,3,4,5-tetrahydrobenz[ c,d]indole-6-carbothioic acid, S-methyl ester (±)-4-amino-1,3,4,5-tetrahydrobenz[c,d]indole-6-carbodithioic acid, n-propyl ester (+)-4-(allylamino)-1,3,4,5-tetrahydrobenz[ c,d]indole-6-carbodithioic acid, ethyl ester (±)-4-(di-n-propylamino)-1,3,4,5-tetrahydrobenz[ c,d]indole-6-carbothioic acid, S-methyl ester (−)-4-(methylamino)-1,3,4,5-tetrahydrobenz[ c,d]indole-6-carboxylic acid, n-propyl ester (+)-4-amino-1,3,4,5-tetrahydrobenz[c,d]indole- 6-carboxylic acid, methyl ester (±)-4-(diethylamino)-1,3,4,5-tetrahydrobenz[c,d] indole-6-carboxylic acid, n-propyl ester maleate (±)-4-(dimethylamino)-1,3,4,5-tetrahydrobenz[c,d] indole-6-carboxylic acid, methyl ester (−)-4-(methylisopropylamino)-1,3,4,5-tetrahydrobenz[ c,d]indole-6-carbothioic acid, O-methyl ester (+)-4-(di-5-propylamino)-1,3,4,5-tetrahydrobenz[ c,d]indole-6-carboxaldehyde (±)-4-(ethylamino)-1,3,4,5-tetrahydrobenz[ c,d]indole-6-carbothioic acid, S-methyl ester (±)-4-(methylethylamino)-1,3,4,5-tetrahydrobenz[ c,d]indole-6-carboxylic acid, ethyl ester (+)-4-(sec.-butylamino)-1,3,4,5-tetrahydrobenz[ c,d]indole-6-carbodithioic acid, methyl ester The compounds of the present invention can be prepared by the following process. A 4-amino-6-bromotetrahydrobenz[ c,d]indole is converted to a 1-potassium- 6-lithium substituted derivative which is treated with an appropriate electrophile. The compound thus prepared may require deblocking to provide a compound of the invention. This reaction may be represented by the following Scheme I:

Reaction Scheme 1

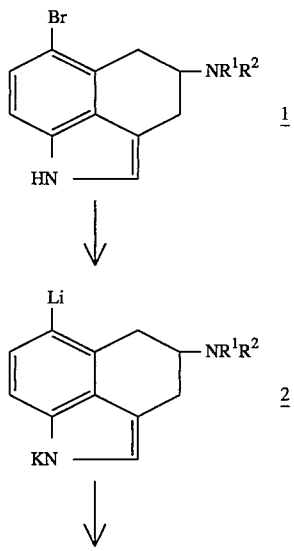

-continued
Reaction Scheme 1

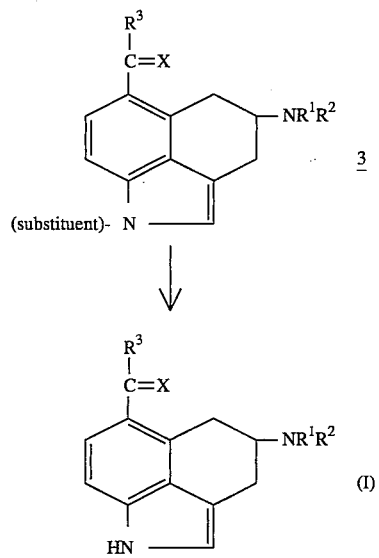

wherein $R^1$, $R^2$, $R^3$ and X are as defined above.

According to this process, a 4-amino-6-bromotetrahydrobenz[ c,d]indole 1 is combined with an equimolar to slight excess amount of potassium hydride in diethyl ether. The reagents are generally combined at a cold temperature, typically in the range of about −20° C. to about 10° C., preferably at about 0° C.. The resulting mixture is next cooled to a temperature in the range of about −100° C. to about −60° C., preferably at about −78° C., and combined with a lithiating reagent, preferably in at least a two molar excess amount. Suitable lithiating reagents include sec.-butyllithium and t-butyllithium, which is preferred. The reaction is substantially complete after about 10 minutes to about 6 hours when conducted at a temperature in the range of about −100° C. to about −20° C., preferably at about −60° C. to about −40° C.

The 4-amino-6-lithiumtetrahydrobenz[c,d]indole 2 thus prepared is next converted to the 1,6-disubstituted- 4-aminotetrahydrobenz[c,d]indole 3 upon reaction with an appropriate electrophile such as $R^3C(=X)Y$ wherein X is defined above and Y is a good leaving group such as cyano. Typically, a solution of the compound 2 at a temperature in the range of about −100° C. to about −60° C., preferably at about −80° C., is added to a solution of this reagent in a mutual solvent. Typically at least a four molar excess amount of the electrophile is employed in the reaction. The reaction is substantially complete after about 10 minutes to about 2 hours when conducted at a temperature in the range of about −40° C. to about 10° C. The desired compound is purified by quenching the reaction mixture with, for example, ice water. The mixture is washed with a water-immiscible organic solvent. The organic phase is extracted with acid, and the aqueous phases are combined, made basic and the desired compound extracted with a water immiscible organic solvent. The organic solvent is then concentrated, typically under vacuum, and the desired compound 3 is further purified, if necessary, by standard procedures.

If any nitrogen atoms are acylated in the foregoing reactions including the 1-amino group as indicated by the term "substituent" in compound 3, the compounds of Formula (I) can be prepared according to standard deblocking conditions. Deblocking can generally be accomplished by treatment with a base, such as ammonium hydroxide or potassium carbonate in a protic solvent such as alcohol or water. The desired compound is isolated by standard conditions and purified by crystallization from common solvents or column chromatography over solid supports such as silica gel or alumina.

In a preferred method, the halogen-metal exchange can be facilitated by first providing a triisopropylsilyl group on the 1-position of the indole. This can be accomplished by initially treating the indole with a base such as potassium hydride followed by treatment with a triisopropylsilyl halide such as chloride or with triisopropylsilyl triflate. After the halogen-metal exchange and substitution reaction described above, the triisopropylsilyl group ("substituent" in indole 3) can be removed using a conventional desilylating agent such as tetrabutylammonium fluoride or cesium fluoride.

Thiocarboxylic acid esters defined by Formula (I) wherein X is sulfur form another important group of compounds that are a further embodiment of this invention. The thiocarboxylic acid esters of the invention may be prepared by thiating the corresponding carboxylic acid ester or thioester. Any of several thiating agents can be employed in this reaction including phosphorous pentasulfide. Another thiating agent is Lawesson's Reagent, which is 2,4-bis(4-methoxyphenyl)-1,3-dithia-2,4-diphosphetane-2,4-disulfide. This thiating agent and its general uses are described in detail in *Tetrahedron Letters*, 21, 4061 (1980). The thiation reaction is preferably carried out by combining approximately equimolar quantities of the carboxylic acid ester and thiating agent in a mutual organic solvent such as toluene or dioxane. The reaction is generally complete within about 1 hour to about 10 hours when carried out at a temperature of about 50° C. to about 150° C. The thiocarboxylic acid esters thus formed can be isolated and purified by normal methods such as crystallization and the like.

The thiocarboxylic acid esters of Formula (I) can also be prepared by reacting the 4-amino-6-lithiumtetrahydrobenz[c,d]indole 2, prepared as described above, with a thiocarbonyl reagent such as carbon disulfide or thiocarbonyl-1,1'-diimidazole, which can then be converted to a compound of Formula (I) by reaction with the desired electrophile as described above.

The compounds of Formula (I) wherein the 6-position contains a carboxylic acid group can be prepared by hydrolyzing the 6-CN derivatives as described by Flaugh in U.S. Pat. No. 4,576,959. The 6-carboxylic acid derivatives can also be prepared by contacting the 6-lithium substituted derivative 2 with carbon dioxide. The 6-carboxylic acids can be used as intermediates to certain compounds of the invention. For example, the 6-carboxylic or 6-thiocarboxylic acids can be reacted with a reagent $R^3XH$ (wherein $R^3$ is other than hydrogen and X is oxygen or nitrogen) and a coupling reagent, for example any of the type of coupling reagents commonly employed in the synthesis of peptides, and the desired ester, amide, thioamide or thioester isolated. Examples of such coupling reagents include carbodiimides, such as N,N'-dicyclohexylcarbodiimide, N,N'-diisopropylcarbodiimide or N,N'-diethylcarbodiimide; the imidazoles such as carbonyl diimidazole as well as reagents such as N-ethoxycarbonyl-2-ethoxy-1,2-dihydroquinoline (EEDQ).

The compounds of Formula (I) wherein $R^3$ is hydrogen form the carboxaldehydes of the invention and can be prepared by reducing a 4-amino-6-cyanotetrahydrobenz[c,d]indole with a hydride reducing agent such as diisobutylaluminum hydride, and isolating the desired compound according to standard procedures.

The pharmaceutically acceptable salts of the invention are typically formed by reacting an amine of the invention with an equimolar or excess amount of acid. The reactants are generally combined in a mutual solvent such as diethyl ether or benzene, and the salt normally precipitates out of solution within about one hour to about 10 days and can be isolated by filtration.

The 4-amino-6-bromo (and cyano and carboxylic acid)tetrahydrobenz[c,d]indole starting materials used to prepare the compounds of the invention are known compounds readily prepared by prior art processes. The following process depicted as Reaction Scheme 2 disclosed in U.S. Pat. No. 4,576,959 of Flaugh can be used.

Reaction Scheme 2

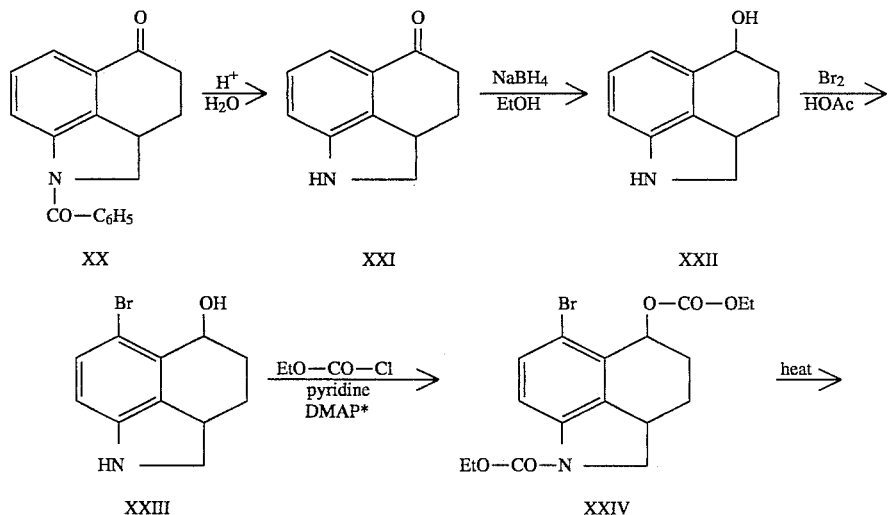

Reaction Scheme 2 -continued

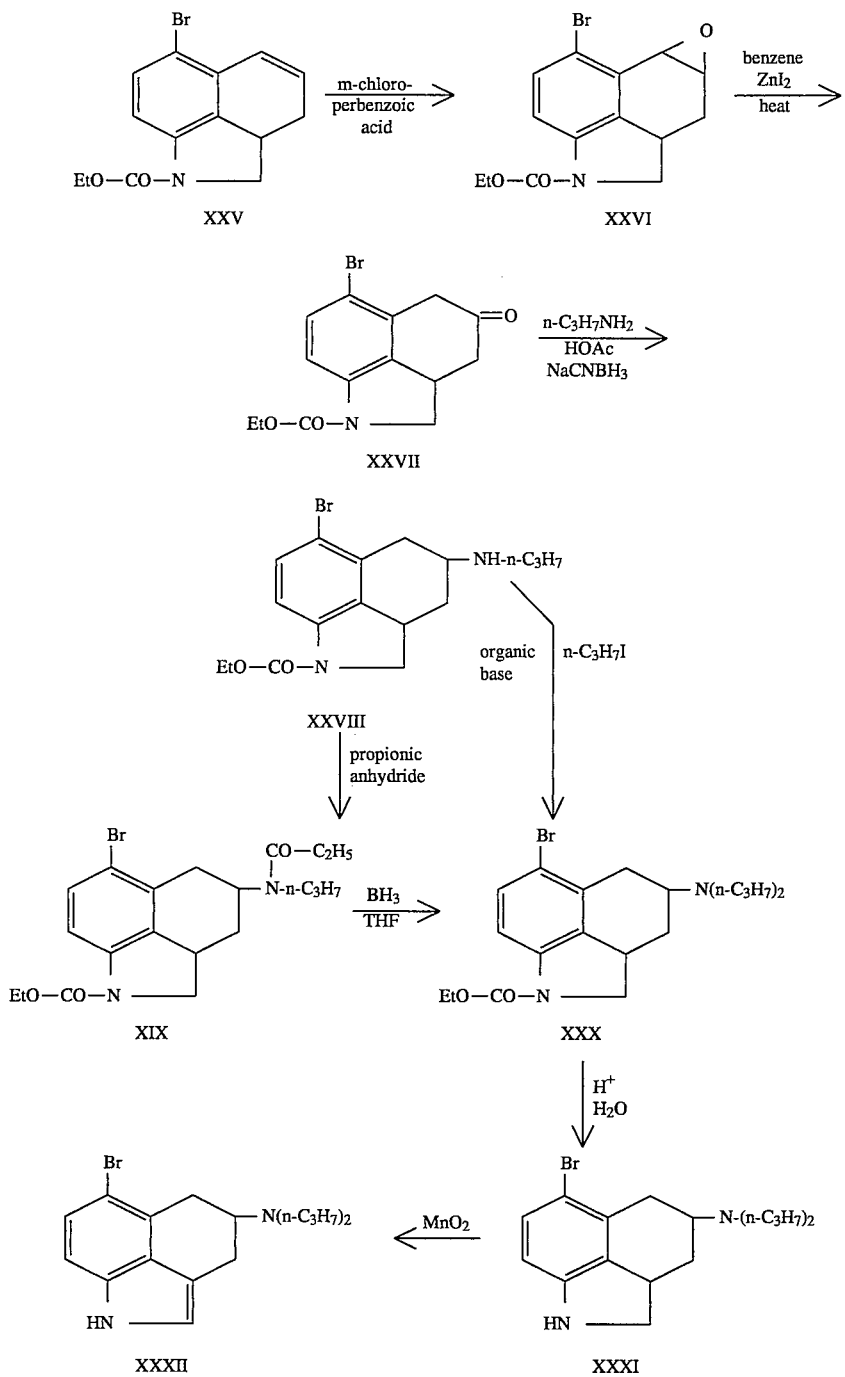

In the above reaction scheme, 1-benzoyl-5-oxo- 1,2,2a,3, 4,5-hexahydrobenz[c,d]indole (XX) [from Kornfeld et al., *Journal of the American Chemical Society*, 78, 3887 (1956) compound 4] is hydrolyzed in acid to 5-oxo- 1,2,2a,3,4,5-hexahydrobenz[c,d]indole (XXI) (compound 10 of Kornfeld et al. when R is H). The 5-ketone is reduced to a 5-hydroxyl [(±)-5-hydroxy-1,2,2a,3,4,5-hexahydrobenz[ c,d]indole (XXII) with an alkali metal borohydride or aluminumhydride in a mutual inert solvent. Bromination in acetic acid yields the (±)-6-bromo-5-hydroxy derivative (XXIII). This compound is then reacted with 2 moles of ethyl chloroformate to yield a (±)-1-ethoxycarbonyl-5-ethoxycarbonyloxy-6-bromo-1,2,2a, 3,4,5-hexahydrobenz[c,d]indole (XXIV). This double acylation is conveniently carried out in pyridine solution (though other inert solvents may be used) containing an organic base catalyst such as dimethylaminopyridine (DMAP). Heating the 5-ethoxy carbonyloxy compound results in dehydration to produce 1-ethoxycarbonyl-6-bromo-1,2,2a,3-tetrahydrobenz[c,d]indole (XXV). Epoxidation of the double bond using, conveniently, m-chloroperbenzoic acid or other peracid to yield the corresponding 4,5-epoxy, 1-benzoyl derivative. Rearrangement of the epoxide on heating with $ZnI_2$ yields the 4-oxo derivative (XXVII). Reductive amination with n-propylamine and $NaCNBH_3$ yields (±)-1-ethoxycarbonyl-4 -n-propylamino-6-bromo-1,2,2a,3,4,5-hexahydrobenz[c,d]indole (XVIII). This secondary amine can then be alkylated with propionic anhydride and the N-propionyl group reduced with $BH_3$ or $NaCNBH_3$ in trifluoroacetic acid (TFA) to yield the 4-di-n-propyl compound, (±)-1 -ethoxycarbonyl-4-di-n-propylamino-6-bromo-1,2,2a,3,4,5hexahydrobenz[ c,d]indole (XXX). Alternatively, the secondary amine XXVIII can be alkylated as with n-propyliodide in the presence of an organic base to yield XXXI directly. Finally, hydrolysis of the 1-ethoxycarbonylamide yields XXXI, oxidation of which with $MnO_2$ or with N-chlorosuccinimide in the presence of dimethyl sulfide and triethylamine yields a 2,2a-didehydro derivative (XXXII). The ultimate product of this reaction (XXXII) is the desired intermediate (±)-4-di-n-propylamino- 6-bromo-1,3,4,5-tetrahydrobenz[c,d]indole.

Reaction of the thus-formed 6-bromo derivative with cuprous cyanide or an alkali or alkaline earth cyanide and cuprous iodide in 1-methyl-2-pyrrolidone solution yields the 6-cyano derivative, hydrolysis of which with base (KOH, NaOH) in a lower alkanol yields (±)-4-di-n-propylamino-6-carboxamido-1,3,4,5-tetrahydrobenz[ c,d]indole. Replacement of the 6-bromo with CN can be carried out on the indoline (XXXI) as well as on the indoline (XXXII).

The above reaction sequence has been illustrated with respect to the preparation of a 4-di-n-propyl derivative. It will be apparent to those skilled in the art that substitution of other $C_1$–$C_4$ alkyl amines such as methyl or ethyl amine or allyl amine for n-propyl amine in the preparation of XXVIII would yield a 4-methyl, ethyl or allyl amino group. Likewise the thus formed secondary amine could be acylated (XXVIII where the amine group is n-propyl but could be methyl, ethyl, allyl etc.) with formic, acetic, acrylic or propionic acid and the N-acyl group reduced to an alkyl or allyl group to form a compound of the formula

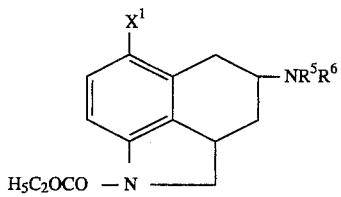

wherein $X^1$ is $NO_2$, I or Br, and $R^5$ and $R^6$ are individually $C_1$–$C_4$ alkyl or allyl. It will be noted that the above procedure provides an easy route to unsymmetrically substituted C-4 tertiary amines.

Alternatively, the secondary amine (XXVIII where the amine group is n-propyl (but could be $C_1$–$C_4$ alkyl or allyl) can be directly alkylated with $CH_3I$, $C_2H_5I$, n-propyl iodide, etc. or allyl bromide to yield the same tertiary amine (XXXa).

In an alternative preparation, the 6-iodo derivatives can be prepared. This can be accomplished by the use of iodine and orthoperiodic acid in the presence of an acid such as sulfuric acid or trifluoroacetic acid in a solvent such as aqueous acetic acid. It may be preferred to iodinate the non-halogenated 4-amino-hexahydrobenz[c,d]indole analog of XXVIII. The 4-amino group of the iodo derivative can be alkylated or acylated as desired using common methods for accomplishing such reactions. For example, alkyl groups can be added to the 4-amino substituent by alkylation with the appropriate alkyl halide as discussed by Morrison and Boyd, Chapter 22, *Organic Chemistry*, Third Edition, Allyn and Bacon, Boston, 1973. It can also be produced by acylation followed by reduction to the amine. This is a method for producing an unsymmetrically substituted 4-amino substituent. The iodination can be accomplished before the alkylation or acylation of the 4-amino group.

Although an ethoxycarbonyl blocking group is depicted for derivative (XXIV) and subsequent derivatives in Reaction Scheme 2, it is contemplated that other blocking groups such as benzoyl trifluoroacetyl, trichloroethoxycarbonyl and the like can be used for the 1-amino group.

6-Ester or 6-amide derivatives can be prepared using palladium-catalyzed carbonylation of the iodo derivatives of the formula

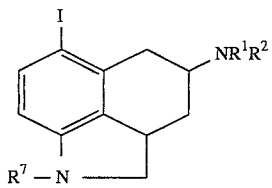

These reactions involve the use of a palladium catalyst with carbon monoxide and an alcohol or an amine to form the respective ester or amide from an aryl halide. These reactions are disclosed in the following articles: Schoenberg and Heck, *Journal of Organic Chemistry*, 39, p 3325 (1974); and Schoenberg, Bartoletti, and Heck, *Journal of Organic Chemistry*, 39, p 3318 (1974). Preferably the 1-nitrogen is blocked with a protecting group $R^7$ such as a benzoyl group. The more reactive these substituents are then the more readily removable the 1-amino-protecting group should be. For example, when 6-alkoxycarbonyl derivatives are prepared, it may be preferred to use a 1-amino protective group such as the $Cl_2CCH_2OCO$- moiety instead of benzoyl. Depending upon the desired final product, the 4-amino group can be protected with a readily removable blocking group such as benzoyl when $R^1$ and/or $R^2$ is hydrogen. Amino blocking groups including acyl groups such as formyl, acetyl, trifluoroacetyl and the like can be introduced using methods disclosed by T. W. Greene in Chapter 7 of *Protective Groups in Organic Synthesis*, John Wiley and Sons, New York, 1981, and by J. W. Barton in Chapter 2 of *Protective Groups in Organic Chemistry*, J. F. W. McOmie, ed., Plenum Press, New York, 1973. When $R^1$ or $R^2$ is alkyl or allyl it is preferred that the 4-amino group be alkylated before the carbonylation is accomplished. For example, when $R^1$ is hydrogen and $R^2$ is isopropyl and $R^7$ is benzoyl, XXXIII can be reacted with carbon monoxide and methanol using bis(triphenylphosphine)palladium chloride as a catalyst at about 70° C. to provide the 6-methoxycarbonyl derivative.

Alternatively, 1-benzoyl-4-amino-1,2,2a,3,4,5-hexahydrobenz[ c,d]indole can be prepared, for example as described by Bach et al. in U.S. Pat. No. 4,110,339 (1978). The 6-iodo derivative can be prepared as described above. The 4-amino group can then be alkylated or protected depending on the final product desired. The iodo derivative can be subjected to the carbonylation reactions described above. When the benzoyl group is used as a blocking agent for the 1-amino group, butyl lithium can be conveniently used to replace the benzoyl with a hydrogen on the 1-amino group for the 6-substituted primary carboxamides.

In a further procedure, the 4,5-epoxide of formula XXXIV below disclosed by Leanna et al. in *Tetrahedron Letters*, 30, No. 30, p 3935 (1989) can be converted to the corresponding aziridine, for example by reaction with 1-phenylethylamine to form an amino alcohol followed by contacting with triethylamine and methanesulfonyl chloride in dichloromethane. The aziridine can be hydrogenolyzed using a catalyst such as palladium to produce 1-benzoyl-4-amino-hexahydrobenz[c,d]indole. This can be used to provide the bromo or iodo derivatives as discussed hereinabove.

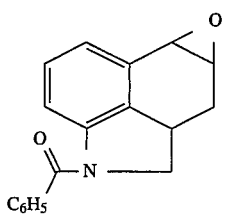

XXXIV

Formation of the aziridine affords a convenient route for providing substantially pure enantiomers of compounds of Formula I. A substantially pure enantiomer of an amine containing at least one chiral center, for example (S)-1-phenylethylamine, can be reacted with the epoxide XXXIV to form the amino alcohol. The diastereomers of the amino alcohol can be separated by known means such as chromatography or crystallization to afford the substantially pure enantiomers. The amino alcohol can be used to form the aziridine in the procedure described hereinabove.

The hexahydrobenz[c,d]indoles described hereinabove can be converted to the corresponding 1,3,4,5-tetrahydrobenz[c,d]indole by oxidation (dehydrogenation) for example with manganese dioxide, N-chlorosuccinimide in the presence of dimethylsulfide, palladium on carbon in methanol, benzene selenenic anhydride and the like. When a primary 4-amino substituted indole is being prepared, it may be desirable to block the 4-amino group with for example an acyl group prior to the oxidation.

The 1,2,2a, 3,4,5-hexahydrobenz[cd]indoles with substituents in the 4- and 6-positions corresponding to Formula I hereinabove, as well as hexahydrobenz[cd]indoles with substituents in the 6-position corresponding to X in Formula IV of Flaugh in U.S. Pat. No. 4,576,959, have been found to be useful serotonin agonists. It has been found that one enantomer can have substantially greater activity than the other enantiomer. This is to be contrasted with the tetrahydrobenz[cd]indoles in which substantial differences have not been observed. In particular (2a-S, 4-R)-4-(di-n-propylamino)-1,2,2a,3,4,5 -hexahydrobenz[cd]indole-6-carboxamide has been found to have substantially greater binding activity for 5HT1A receptors than the (4a-R, 4-S)-diastereomer.

The following Examples further illustrate the compounds of the present invention and methods for their synthesis. The Examples are not intended to be limiting to the scope of the present invention in any respect and should not be so construed.

EXAMPLE 1

(±)-4-(Di-n-propylamino)-1,3,4,5-tetrahydrobenz[c,d]indole-6-carboxylic acid, methyl ester A. Preparation of (±)-1-Methoxycarbonyl-4 -(di-n-propylamino)-1,3,4,5-tetrahydrobenz[c,d]indole-6carboxylic acid, methyl ester A solution of 0.335 grams (g) (1 millimole, mmol) of 4-(di-n-propylamino)-6-bromo-1,3,4,5-tetrahydrobenz[c,d]indole in 5 milliliters (ml) of diethyl ether was added to a suspension of 0.19 g (1.2 mmol) of potassium hydride in a 25% by weight mineral oil dispersion in 25 ml of diethyl ether at about 0° C. The reaction mixture was stirred at 0° C. for 1 hour and cooled to approximately −78° C. with an external dry ice/acetone bath. A solution of 1.7 M t-butyl-lithium (1.5 ml, 2.55 mmol) cooled to about −78° C. was added to the reaction mixture via a cannula. The resulting mixture was allowed to warm to approximately −40° C. and was stirred at that temperature for 2 hours. The turbid mixture was cooled to -78° C. and a solution of 0.34 g (4 mmol) of methyl cyanoformate in 1 ml of diethyl ether was rapidly added. The mixture was allowed to warm to about 0° C. and was quenched with ice water. The mixture was extracted with diethyl ether. The ether extract was extracted with 1 molar (M) phosphoric acid. The aqueous solution was treated with an excess amount of a saturated aqueous sodium bicarbonate solution and extracted with methylene chloride. The organic extract was dried over anhydrous sodium sulfate and concentrated under vacuum. The resulting residue was chromatographed over 5 g of silica gel while eluting first with ethyl acetate:toluene (1:9, volume:volume [v:v]) followed by ethyl acetate:toluene (1:1, v:v). Fractions containing the major component were combined and the solvent was evaporated therefrom to provide 261 milligrams (mg) of (±)-1 -methoxycarbonyl-4-(di-n-propylamino)-1,3,4,5-tetrahydrobenz[c,d]indole-6-carboxylic acid, methyl ester.

B. A solution of 261 mg (0.64 mmol) of (±)-1-methoxycarbonyl-4-(di-n-propylamino)-1,3,4,5 -tetrahydrobenz[c,d]indole-6-carboxylic acid, methyl ester in 10 ml of methanol was added to a solution of 2.0 g of potassium carbonate in 10 ml of water and 20 ml of methanol. The resulting mixture was stirred at room temperature for approximately 1 hour and a thin layer chromatograph indicated that only a trace of starting material remained. The reaction mixture was diluted with an aqueous saturated sodium chloride solution and extracted several times with methylene chloride. The organic extracts were combined and washed with an aqueous sodium chloride solution and dried over anhydrous sodium sulfate. The organic phase was concentrated under vacuum to dryness to provide a crystalline residue which was recrystallized from toluene/hexane to provide 154 mg of (±)-4-(di-5-propylamino)- 1,3,4,5-tetrahydrobenz[c,d]-indole-6-carboxylic acid, methyl ester. mp=132°–132.5° C.

Analysis: ($C_{19}H_{26}N_2O_2$)

Theory: C, 72.58; H, 8.34; N, 8.91;

Found: C, 72.83; H, 8.39; N, 8.88.

NMR (300 MHz, $CDCl_3$): δ 0.91 (triplet, 6H); 1.49 (sextet, 4H); 2.58 (sextet, 4H); 2.78 (triplet, 1H); 3.00 (quartet, 1H) ; 3.03 (triplet, 1H); 3.23 (multiplet, 1H); 3 .81 (quartet, 1H); 3.91 (singlet, 3H); 6.88 (singlet, 1H ); 7.14 ( doublet, 1H ); 7.84 (doublet, 1H); 8.02 (singlet, 1H).

EXAMPLE 2

(±)-4-(Di-n-propylamino)-1,3,4,5-tetrahydrobenz[c,d]indole-6-carboxylic acid, ethyl ester A. Preparation of (±)-1-Ethoxycarbonyl-4 -(di-n-propylamino)-1,3,4,5-tetrahydrobenz[c,d]indole-6-carboxylic acid, ethyl ester A solution of 0.335 g (1 mmol) of 4-(di-n-propylamino)-6-bromo-1,3,4,5-tetrahydrobenz[c,d]indole in 5 ml of diethyl ether was added to a suspension of 0.19 g (1.2 mmol) of potassium hydride in a 25% by weight mineral oil dispersion in 25 ml of diethyl ether at about 0° C. The reaction mixture was stirred at 0° C. for 1 hour and cooled to about −78° C. with an external dry ice/acetone bath. A solution of 1.7 M t-butyllithium (1.5 ml, 2.55 ml) cooled to −78° C. was added to the reaction mixture via a cannula. The resulting mixture was allowed to warm to about −40° C. and held there for 2 hours. The resulting turbid mixture was cooled to about −78° C. To this mixture was added a solution of 0.4 g (4 mmol) of ethyl cyanoformate in 1 ml of diethyl ether. The reaction mixture was warmed to about 0° C. and quenched with ice water. The mixture was washed with diethyl ether and the ether extract was extracted with 1M phosphoric acid. The aqueous solutions were combined and treated with an aqueous sodium bicarbonate solution and extracted with methylene chloride. The methylene chloride extract was dried over anhydrous sodium sulfate and concentrated under vacuum to provide 0.44 g of a residue. The residue was chromatographed over 5 g of silica gel using ethyl acetate:toluene (1:9, v:v) as the eluant. Fractions containing the major component were combined and the solvent was evaporated therefrom to provide 164 mg of the desired compound (±)-1-ethoxycarbonyl-4-(di-n-propylamino)-1,3,4,5-tetrahydrobenz[c,d]indole-6-carboxylic acid, ethyl ester.

B. A solution of 164 mg (0.41 mmol) of (±)-1-ethoxycarbonyl-4-(di-n-propylamino)-1,3,4,5-tetrahydrobenz[c,d]indole-6-carboxylic acid, ethyl ester in 10 ml of methanol was added slowly to a solution of 2.0 g of potassium carbonate in 10 ml of water and 20 ml of methanol. The reaction mixture was stirred at room temperature for approximately 1 hour and diluted with an aqueous sodium chloride solution and extracted with methylene chloride. The organic extracts were combined, dried over anhydrous sodium sulfate and concentrated under vacuum to provide 149 mg of residue. The residue was recrystallized from toluene/hexane to provide 165 mg of (±)-4-(di-n-propylamino)-1,3,4,5-tetrahydrobenz[c,d]-6-carboxylic acid, ethyl ester. mp=116.5°–117° C.

Analysis: ($C_{20}H_{28}N_2O_2$)

Theory: C, 73.14; H, 8.59; N, 8.53;

Found: C, 72.86; H, 8.77; N, 8.54.

NMR (300 MHz, $CDCl_3$): δ 0.91 (triplet, 6H); 1.42 (triplet, 3H); 1.49 (sextet, 4H); 2.58 (triplet, 4H); 2.78 (triplet, 1H); 3.00 (quartet, 1H); 3.03 (triplet, 1H); 3.23 (multiplier, 1H,); 3.83 (quartet, 1H); 4.36 (multiplet, 2H); 6.88 (singlet, 1H); 7.14 (doublet, 1H); 7.84 (doublet, 1H); 8.04 (singlet, 1H).

EXAMPLE 3

(±)-4-(Dimethylamino)-1,3,4,5-tetrahydrobenz[c,d]indole- 6-carboxaldehyde

To a suspension of 0.9 g (3.96 mmol) of (±)-4 -(dimethylamino)-6-cyano-1,3,4,5-tetrahydrobenz[c,d]indole in 10 ml of benzene stirred at room temperature under a nitrogen atmosphere was added 8.1 ml (8.1 mmol) of 1M diisobutylaluminum hydride in toluene dropwise. The reaction mixture was stirred at about 50° C. for 6 hours. The mixture was cooled to room temperature and a solution of 1.0 ml of methanol in 4.5 ml of toluene was added to dissolve the precipitate that had formed. Next, 1.0 ml of water in 4.5 ml of methanol was added, and the resulting mixture was added to ice cold 0.5M hydrochloric acid and shaken. The aqueous layer and a 0.5M hydrochloric acid extraction of the separated organic phase were combined and made basic with 2M sodium hydroxide. The aqueous phase was extracted with methylene chloride, and the organic phase was washed with a saturated sodium chloride solution, dried over anhydrous sodium sulfate and concentrated under vacuum to provide an oil. The oil was chromatographed employing ethyl acetate:methanol (19:1, v:v) as the eluant. Fractions containing the major component were combined and the solvent was evaporated therefrom to provide 0.5 g of the title compound following recrystallization from ethyl acetate/toluene. mp=163° C.

Analysis: ($C_{14}H_{16}N_2O$)

Theory: C, 73.66; H, 7.06; N, 12.27;

Found: C, 73.50; H, 7.02; N, 12.17.

NMR (300 MHz, $CDCl_3$): 6 2.48 (singlet, 6H); 2.86 (quartet, 1H); 3.08 (multiplet, 2H); 3.19 (multiplet, 1H); 3.86 (broad doublet, 1H); 6.95 (singlet, 1H); 7.25 (doublet, 1H); 7.66 (doublet, 1H); 8.31 (singlet, 1H); 10.28 (singlet, 1H).

EXAMPLE 4

(±)-4-(Di-n-propylamino)-1,3,4,5-tetrahydrobenz[c,d]indole-6-carboxaldehyde

A 100 ml three neck round bottom flask under a nitrogen atmosphere was charged with 0.176 g (1.1 mmol) of 25% potassium hydride in mineral oil which had been washed with heptane. To the flask was added 40 ml of diethyl ether and the mixture was cooled to about 0° C. To the mixture was added a solution of 0.335 g (1.0 mmol) of (±)-4-(di-n-propylamino)-6-bromo-1,3,4,5-tetrahydrobenz[c,d]indole in 10 ml of diethyl ether over a period of about 5 minutes. The mixture was stirred at about 0° C. for one hour, and for three hours at room temperature. The mixture was cooled to about −78° C. with an external dry ice/acetone bath and 1.47 ml of 1.7M t-butyllithium was added dropwise over a period of about 10 minutes. The mixture was warmed to about −50° C. over about two hours. The mixture was again cooled to about −78° C. and 0.193 ml of dry DMF in 10 ml of diethyl ether was added. The mixture was stirred at −78° C. for 30 minutes, warmed to room temperature, and stirred overnight. To the mixture was added 50 ml of water and 25 ml of diethyl ether. The mixture was washed twice with 50 ml portions of water. The organic phase was dried over anhydrous sodium sulfate, filtered and concentrated under vacuum to provide 0.17 g of a brown oil. The oil was chromatographed over silica gel employing ethyl acetate:toluene:triethylamine (42:42:16, v:v:v) as the eluant. Fractions containing the major component were combined and the solvent was evaporated therefrom to provide 0.19 g of (±)-4-(di-n-propylamino)-1,3,4,5-tetrahydrobenz[c,d]indole-6-carboxaldehyde as a yellow oil.

NMR (300 MHz, $CDCl_3$): δ 0.95 (triplet, 6H); 1.50 (multiplet, 4H); 2.60 (triplet, 4H); 3.10 (multiplet, 4H); 3.80 (doublet, 1H); 7.00( multiplet, 3H); 8.3 (singlet, 1H); .".0.3 ( singlet, 1H).

EXAMPLE 5

(±)-(N-Methyl)-4-(di-n-propylamino)-1,3,4,5-tetrahydrobenz[c,d]indole-6-carboxamide A solution of 0.335 g (1 mmol) of 4-(di-n-propylamino)-6-bromo-1,3,4,5-tetrahydrobenz[c,d]indole in 5 ml of diethyl ether was added to a suspension of 0.20 g (1.25 mmol) of potassium hydride in a 24% by weight mineral oil dispersion in 25 ml of diethyl ether at about 0° C. The reaction mixture was stirred at 0° C. for 1 hour and cooled to approximately −78° C. with a dry ice/acetone bath. A solution of 1.54M t-butyllithium (1.7 ml, 2.62 mmol) in pentane was gradually added to the reaction mixture. The resulting mixture was allowed to warm to approximately −40° C. and was stirred at that temperature for 2 hours. The turbid mixture was again cooled to approximately −78° C. Using a double-tipped needle, the mixture was transferred to a flask containing 0.25 ml (4.24 mmol) of methyl isocyanate in 10 ml of THF that was cooled with dry ice. After stirring for an additional 20 minutes, 10 ml of methanol were added; and the temperature was allowed to warm to 25° C. The mixture was treated with water. The aqueous layer was extracted with fresh ether, and the combined ether solutions were then extracted with 1M phosphoric acid. This aqueous solution was allowed to stand for 20 minutes and was then basified to pH 10 using 5M sodium hydroxide solution. Extraction with methylene chloride followed by evaporation of this solvent gave 0.34 g of a viscous oil. Chromatography of this material over 5 g of florisil using successively 1:1 ethyl acetate/toluene, ethyl acetate, and 3% methanol in ethyl acetate afforded product which, after crystallization from toluene, weighed 66 mg (27% yield). mp 161.5°–163.5° C. A sample was recrystallized from toluene for elemental analysis.

Analysis: ($C_{19}H_{27}N_3O$)

Theory: C, 72.81; H, 8.68; N, 13.41

Found: C, 72.75; H, 8.84; N, 13.20

NMR (300 MHz, $CDCl_3$) δ 0.90 (t, 6H, $CCH_3$), 1.48 (sextet, 4H, $CH_2Me$), 2.56 (sextet, 4H, $CH_2Et$), 2.79 (t, 1H, 3α-H), 2.93–2.08 (mult, 2H, 3β-H & 5α-H), 3.03 (d, 3H, $NCH_3$), 3.22 (mult, 1H, 4β-H), 3.46 (qt, 1H, 5β-H), 5.82 (br s, 1H, NHMe), 6.89 (s, 1H, 2-H), 7.12 (d, 1H, 8-H), 7.33 (d, 1H, 7-H), 7.99 (s, 1H, 1-H).

EXAMPLE 6

(±)-(N,N-Diethyl)-4-(di-n-propylamino)-1,3,4,5-tetrahydrobenz[c,d]indole-6-carboxamide A. Preparation of (i)-6-bromo-1-triisopropylsilyl- 4-(di-n-propylamino)-1,3,4,5-tetrahydrobenz[c,d]indole To a suspension of 1.25 g (7.50 mmol) of potassium hydride (24% dispersion in mineral oil) in 50 ml of THF at 0° C. was added a solution of 2.00 g (5.97 mmol) of 6-bromo-4-( di-n-propylamino )-1,3,4,5 -tetrahydrobenz[c,d]indole in 2 ml of THF. After stirring for 40 minutes, an addition of 1.90 ml (7.18 mmol) of triisopropylsilyl triflate was made. Stirring was continued for another 30 minutes. The mixture was then poured in cold $NaHCO_3$ solution, and the product was extracted into $CH_2Cl_2$. This extract was washed with NaCl solution and dried over $Na_2SO_4$. Evaporation of the $CH_2Cl_2$ left a brown oil which was chromatographed over 50 g of silica gel using toluene followed by 1:3 EtOAc/toluene. The silylated product from the column was isolated as a light brown oil in quantitative yield.

B. Preparation of (±)-(N,N-diethyl)-1-triisopropylsilyl-4-(di-n-propylamino)-1,3,4,5-tetrahydrobenz[c,d]indole-6-carboxamide A solution of of 0.30 g (0.65 mmol) of the 1-silylated compound from Example 6A in 10 ml of diethyl ether was stirred at −65° C. as 0.90 ml (1.39 mmol) of 1.54 M t-butyllithium (in pentane) was added. After stirring at −70° C. for another 30 minutes, a rapid addition of 0.17 ml (1.34 mmol) of N,N-diethylcarbamyl chloride was made. The mixture was allowed to warm to 0° C. It was then poured into 50 ml of cold $NaHCO_3$ solution, and the product was extracted into diethyl ether. This extract was washed with NaCl solution and dried over $Na_2SO_4$. Evaporation of the ether left an oil which was chromatographed over 5 g of florisil using successively toluene, 1:19 EtOAc/toluene, and 1:3 EtOAc/toluene. Early product containing fractions were slightly impure. This impure material (100 mg) was rechromatographed over 3 g of silica gel using toluene followed by 1:9 EtOAc/toluene. The combined product crystallized upon removal of the solvents. The crystalline amide weighed 0.22 g (71% yield), mp 84°–87° C.

C. A solution of 0.20 g (0.41 mmol) of the amide product from Example 6B in 5.0 ml of kiethylether at 0° C. was treated with 1.0 ml of 1M tetrabutylammonium fluoride in THF. After stirring for 15 minutes the solution was poured into 15 ml of water containing 0.25 g of tartaric acid. This solution was washed with $CH_2Cl_2$, and these washings were extracted with fresh dil. tartaric acid solution. The combined aqueous solutions were basified with 5N NaOH solution, and the product was extracted with $CH_2Cl_2$. After drying the extract over $Na_2SO_4$, the solvent was evaporated and the residual oil was chromatographed over 3 g of silica gel using successively toluene, 1:19 EtOAc/toluene, and EtOAc. The product from the column was a viscous oil weighing 0.13 g (88% yield).

Analysis: ($C_{22}H_{33}N_3O$)

Theory: C, 74.33; H, 9.36; N, 11.82

Found: C, 74.12; H, 9.32; N, 11.94

NMR (300 MHz, $CDCl_3$) δ 0.89 (t, 6H, $CCH_3$ of NPr), 1.02 (br t, 3H, $CCH_3$ of NEt), 1.29 (br t, 3H, $CCH_3$ of NEt), 1.46 (sextet, 4H, $CCH_2Me$), 2.53 (t, 4H, $CH_2Et$), 2.79 (t, 1H, 3α-H), 2.89 (mult, 1H, 3β-H), 2.97 (t, 1H, 5α-H), 2.99 (qt, 1H, 3β-H), 3.24 (mult, 3H, 4β-H & $NCH_2Me$), 3.63 (mult, 2H, $NCH_2Me$), 6.87 (s, 1H, 2-H), 7.02 (d, 1H, 8-H), 7.12 (d, 1H, 7-H), 7.96 (s, 1H, 1-H).

EXAMPLE 7

(2a-R, 4-S)-1-benzoyl-4-(di-n-propyl)amino-6-iodo-1,2,2a,3,4,5-hexahydrobenz[c,d]indole Fifty milliliters of a solution of 1-benzoyl- 4-(di-5-propyl)amino-1,2,2a,3,4,5-hexahydrobenz[cd]indole (approximately 500 mg, approximately 1.4 mmoles) in acetonitrile was placed into a 100 ml flask. The solvent was removed in vacuo to afford a viscous oil. To the oil was added a mixture of acetic acid, water and sulfuric acid (25 ml, 100:20:3 by volume). To the resulting solution was added orthoperiodic acid (96 mg, 0.42 mmoles) and iodine (218 mg, 0.89 mmoles). The reaction mixture was heated to 70° C. and maintained at that temperature, under nitrogen purge, for 25 minutes. The solvent and excess iodine were removed in vacuo. The residue was taken up in water (50 ml). An addition of aqueous sodium hydroxide (5 Normal (N), 15 ml) raised the pH to approximately 12 and caused the precipitation of a solid. The mixture was cooled to approximately 0° C. The solid was filtered, washed with water (3 times, 30 ml each), and dried in vacuo to afford a tan solid (619 mg). This material, provided the following data corresponding to (2a-R,4-S)-1-benzoyl-4-(di-5-propyl)amino-6-iodo-1,2,2a,3,4,5-hexahydrobenz[cd]indole.

($CHCl_3$): 3010 (w), 2961 (m), 2934 (m), 2870 (w), 1638 (s), 1467 (s), 1453 (s), 1382 (s), 1222 (w) $cm^{-1}$

NMR: ($^1H$, ppm, $CDCl_3$): 7.3–7.7 (m, 7H), 4.25 (br m, 1H), 3.65 (t, 1H), 3.30 (m, 1H), 3.20 (m, 1H), 2.80 (dd, 1H), 2.45 (m, 5H), 2.15 (m, 1H), 1.25–1.60 (m, 5H), 0.90 (t, 6H)

M.S.: m/e=448.

Analysis: ($C_{24}H_{29}N_2O$)

Theory C, 59.02; H, 5.98; N, 5.73

Found C, 58.78; H, 6.04; N, 5.68

As noted above, the compounds of this invention are serotonin agonists useful in the enhancement of serotonin function in mammals. As serotonin agonists, the compounds mimic the action of serotonin in mammals.

The compounds have been found to have selective affinity for the 5HT1A receptor in the brain with much less affinity for other receptors. Because of their ability to selectively block 5HT1A receptors, the compounds of Formula (I) are useful in treating disease states which require enhancement of serotonin function to improve, but without the side effects which may be associated with less selective compounds.

strate the serotonin agonist properties of the compounds of the present invention.

In one such experiment the compounds of Examples 1 and 3 were evaluated to determine their ability to affect the 5-hydroxyindoles serotonin and 5-hydroxyindole acetic acid (5HIAA), and serum corticosterone, in vivo. According to this test, Wistar rats each weighing from about 150 g to about 200 g were given a formulation of the test compound in 0.01N HCl at various doses. Sixty minutes later each rat was decapitated and the concentration of serotonin, 5HIAA and serum corticosterone was measured in the whole brain. The results of this experiment are set forth below in Table I.

TABLE I

| | | 5-Hydroxyindoles and Serum Corticosterone | | |
|---|---|---|---|---|
| Compound Evaluated | Dose (mg/kg) | Serotonin (nmoles/g) | 5HIAA (nmoles/g) | Serum Corticosterone (µg/100 ml) |
| Example 1 | 0.1 | 3.22 ± 0.14 | 1.98 ± 0.07* | 14.9 ± 2.4* |
| | 0.3 | 3.38 ± 0.13 | 1.89 ± 0.04* | 39.6 ± 3.5* |
| | 1.0 | 3.52 ± 0.16* | 1.80 ± 0.04* | 44.6 ± 2.6* |
| Example 3 | 0.1 | 3.00 ± 0.06 | 2.50 ± 0.12 | 7.4 ± 1.4* |
| | 0.3 | 3.27 ± 0.14 | 2.88 ± 0.09* | 44.7 ± 1.7* |
| Control | — | 3.09 ± 0.08 | 2.52 ± 0.08 | 3.8 ± 0.6 |

*P < .05

These disease states include anxiety, depression, consumptive disorders such as obesity, alcoholism and smoking, and senile dementia. A pharmaceutically effective amount of a compound of Formula (I) is required to treat the foregoing conditions.

The term "pharmaceutically effective amount", as used herein, represents an amount of a compound of the invention which is capable of enhancing the function of serotonin. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical single dose for prophylactic treatment, however, will contain from about 0.01 mg/kg to about 20 mg/kg of the active compound of this invention when administered orally. Preferred oral doses will be about 0.5 to about 10 mg/kg, ideally about 1.0 to about 5 mg/kg. When a present compound is given orally it may be necessary to administer the compound more than once each day, for example about every eight hours. For IV administration by bolus, the dose will be from about 1.0 µg/kg to about 3000 µg/kg, preferably about 50 µg/kg to about 500 µg/kg.

Several experiments were conducted in order to demon-

A second experiment was conducted evaluating the compound of Example 1 in the foregoing procedure using lower doses. Serum corticosterone was not measured. The results are set forth in Table II.

TABLE II

| | | 5-Hydroxyindoles, nmoles/g | |
|---|---|---|---|
| Compound Evaluated | Dose (mg/kg) | Serotonin | 5HIAA |
| Example 1 | 0 | 3.11 ± 0.04 | 2.42 ± 0.04 |
| | 0.01 | 3.21 ± 0.13 | 2.28 ± 0.04* |
| | 0.03 | 3.09 ± 0.07 | 2.17 ± 0.05* |
| | 0.1 | 3.33 ± 0.08* | 1.94 ± 0.05* |
| | 0.3 | 3.22 ± 0.07 | 1.65 ± 0.09* |
| | 1.0 | 3.02 ± 0.11 | 1.59 ± 0.05* |

*P < .05

The compound of Example 1 was also evaluated to determine its affect on certain brain catecholamines and metabolites. The foregoing procedure was again employed and the concentration of dopamine, 3,4-dihydroxyphenylacetic acid (DOPAC), homovanillic acid (PIVA) and norepinephrine in nanomoles per gram was determined. Dopamine and norepinephrine are catecholamines whereas DOPAC and HVA are dopamine metabolites. These results are set forth below in Table III.

TABLE III

| Compound Evaluated | Dose (mg/kg) | Brain Catecholamines and Metabolites, nmoles/g | | | |
|---|---|---|---|---|---|
| | | Dopamine | DOPAC | HVA | Norepinephrine |
| Example 1 | 0 | 3.80 ± 0.08 | 0.49 ± 0.02 | 0.21 ± 0.01 | 2.16 ± 0.07 |
| | 0.01 | 3.60 ± 0.10 | 0.46 ± 0.02 | 0.19 ± 0.01 | 2.14 ± 0.09 |
| | 0.03 | 3.66 ± 0.04 | 0.51 ± 0.02 | 0.21 ± 0.01 | 1.99 ± 0.04 |
| | 0.1 | 3.80 ± 0.10 | 0.65 ± 0.02* | 0.26 ± 0.01* | 2.07 ± 0.04 |

TABLE III-continued

| Compound Evaluated | Dose (mg/kg) | Brain Catecholamines and Metabolites, nmoles/g | | | |
|---|---|---|---|---|---|
| | | Dopamine | DOPAC | HVA | Norepinephrine |
| | 0.3 | 3.80 ± 0.06 | 0.69 ± 0.01* | 0.26 ± 0.01* | 1.84 ± 0.04* |
| | 1.0 | 4.08 ± 0.07* | 0.81 ± 0.02* | 0.31 ± 0.01* | 1.67 ± 0.05* |

$P < .05$

It is known that a decrease of serotonin turnover in the brain is yet another indicator of serotonin agonist activity. Decreased serotonin turnover is established when 5-hydroxytryptophan (5HTP) accumulation in the brain is diminished after decarboxylase inhibition. In another experiment, the ability of the compound of Example 1 to diminish 5HTP accumulation in rat hypothalamus after decarboxylase inhibition was determined. The test compound was administered by subcutaneous injection at various doses to rats. Thirty minutes later the decarboxylac inhibitor NSD 1015 (m-hydroxybenzylhydrazine) was injected at a dose of 100 mg/kg i.p. Thirty minutes after administration of the inhibitor the rats were killed and the concentration of 5HTP in the hypothalamus measured. The results are set forth below in Table IV.

TABLE IV

| 5HTP Accumulation | |
|---|---|
| Dose of Example 1 (mg/kg) | 5HTP in Hypothalamus (nmoles/g) |
| 0 | 1.18 ± 0.06 |
| 0.01 | 1.31 ± 0.06 |
| 0.03 | 1.09 ± 0.05 |
| 0.1 | 0.80 ± 0.03* |
| 0.3 | 0.81 ± 0.04* |
| 1.0 | 0.82 ± 0.02* |

$*P < .05$

The duration of action of the compound of Example 1 was also evaluated. According to this experiment, 0.3 mg/kg of the compound in 0.1N HCl was administered subcutaneously to rats. The rats were killed by decapitation at various time intervals thereafter and the concentration of serotonin and 5HIAA measured. The results are set forth in Table V.

TABLE V

| Duration of Action | | |
|---|---|---|
| Hours after compound injection | Brain 5-hydroxyindoles (nmoles/g) | |
| (0.3 mg/kg s.c.) | Serotonin | 5HIAA |
| 0 | 4.64 ± 0.16 | 3.64 ± 0.24 |
| 1 | 5.25 ± 0.15* | 2.34 ± 0.05* |
| 2 | 5.17 ± 0.25 | 2.64 ± 0.09* |
| 4 | 4.28 ± 0.10 | 3.14 ± 0.14 |
| 8 | 4.54 ± 0.14 | 3.39 ± 0.09 |
| 24 | 4.32 ± 0.19 | 3.59 ± 0.13 |

$*P < .05$

The compound Example 2 was also evaluated in the experiments set forth above for Example 1. The results generated when the effect of the compound on 5-hydroxyindoles and serum corticosterone was evaluated are set forth in Table VI.

TABLE VI

| 5-Hydroxyindoles and Serum Corticosterone | | | | |
|---|---|---|---|---|
| Compound Evaluated | Dose (mg/kg) | Serotonin (nmoles/g) | 5HIAA (nmoles/g) | Serum Corticosterone (μg/100 ml) |
| Example 2 | 0.1 | 2.66 ± 0.07 | 2.06 ± 0.06* | 5.5 ± 1.0 |
| | 0.3 | 2.81 ± 0.07 | 1.88 ± 0.11* | 7.2 ± 0.7* |
| | 1.0 | 3.29 ± 0.28 | 1.93 ± 0.12* | 40.3 ± 2.0* |
| Control | — | 2.87 ± 0.09 | 2.47 ± 0.04 | 3.8 ± 0.2 |

$*P < .05$

The compound of Example 2 caused no significant change in dopamine or homovanillic acid concentrations when measured in the foregoing experiment, but DOPAC was increased by 16% at the highest dose of compound administered. Norepinephrine was decreased at all three doses (−15%, −23% and −27%, respectively from lowest dose to highest dose).

In yet another experiment, the compound of Example 2 was given at 0.3 mg/kg s.c. at various times before rats were killed. 5HIAA concentration was measured in the hypothalamus. These results are set forth in Table VII.

TABLE VII

| 5HIAA Concentration | | |
|---|---|---|
| Compound Evaluated | Hours after injection 0.3 mg/kg s.c. | 5HIAA in hypothalamus (nmoles/g) |
| Example 2 | 0 | 2.62 ± 0.09 |
| | 1 | 1.81 ± 0.07* (−31%) |
| | 2 | 1.99 ± 0.08* (−24%) |
| | 4 | 2.32 ± 0.17 |
| | 8 | 2.57 ± 0.06 |
| | 24 | 2.36 ± 0.11 |

The compound of Example 1 was also evaluated to determine its ability to bind to the 5HT1A receptor and the spiperone receptor in rat brain. The procedure employed is the same as that set forth by Wong et al. in *J. Neural Transmission* 64, 251–269 (1985). The results are set forth below in Table VIII.

TABLE VIII

| Receptor Binding (IC$_{50}$, nmoles) | | |
|---|---|---|
| Compound Evaluated | 5HT1A | Spiperone |
| Example 1 | 1.1 | 52.7 |
| Example 3 | 103 | 45 |

The compounds of the present invention have also been found to have the ability to treat sexual dysfunction in mammals. As such, yet another embodiment of the present invention is the use of the compounds of Formula (I) for treating sexual dysfunction in mammals suffering from such dysfunction and in need of treatment comprising administering to said mammal a compound of the invention. For oral administration the drug is mixed with one or more standard pharmaceutical excipients, such as starch, and loaded into capsules each containing about 0.1–15 mg of active drug. Dosage levels of from about 0.01–1000 mcg (micrograms)/kg have been found to be effective in improving sexual function, particularly in increasing male potency. The oral-dosage forms would be administered 3–4 times per day, giving a daily dosage range of about 0.3 mcg/kg per day to about 400 mcg/kg per day.

The ability of the compounds of the present invention to affect sexual behavior in male animals was established by the following experiments.

Adult male rats of the Sprague-Dawley strain were used in these studies. The sexual behavior evaluations were conducted at 2-week intervals beginning at 6 months of age and ending at 12 months of age. During the initial screening process, the male rats of various levels of sexual performance were selected for compound testing. These performance levels included male rats that displayed no mounting behavior (Non-Maters); male rats that were able to mount but were unable to ejaculate during the test period (Non-Ejaculators); and male rats that were able to ejaculate during the test period. Prior to treatment with a drug solution, each male rat was required to have at least two consecutive vehicle tests with similar sexual performance. Following each compound testing, additional vehicle tests were performed. In an effort to eliminate behavioral responses with compound treatment that may be due to spontaneous changes in mating performance, a criterion of reversibility of behavioral response with subsequent vehicle treatment was employed. Thus, a valid behavioral response to a drug treatment was arbitrarily set as a response that either did not change from the prior control response or was reversed in the subsequent control test with vehicle.

The mating tests were performed during the dark phase of the lighting cycle using red light illumination. Each behavioral test was initiated with the introduction of a receptive female rat into the arena and was terminated either 30 minutes later or immediately following the first postejaculatory mount. The index of mating performance that was evaluated for the rats capable of ejaculation was ejaculatory latency, defined as the time interval from intromission to ejaculation.

Each male rat was given a solution containing either the vehicle alone in water or the compound of Example 2, (±)-4-(di-n-propylamino)-1,3,4,5-tetrahydrobenz[c,d]indole-6-carboxylic acid, ethyl ester in the same vehicle. Vehicle was made of 1 mM (millimolar) acetic acid and 1 mM ascorbic acid.

The results of this study are set forth below in Table IX. In the Table "N" is the number of animals used to aenerate the data, the average of which is provided. The specific description of the test performed is set forth in the heading of the Table.

TABLE IX

Effects of Example 2 on Sexual Behavior
Of Male Rats - Subcutaneous Administration

|  | Ejaculating Rats (Ejaculatory Latency) | Non-Ejaculating Rats (% Ejaculating) |
|---|---|---|
| Control | 753.6 ± 108.7 | 0.0 (0/12) |
| 10.0 mcg/kg | 591.7 ± 50.7 | 58.3 (7/12) |

TABLE IX-continued

Effects of Example 2 on Sexual Behavior
Of Male Rats - Subcutaneous Administration

|  | Ejaculating Rats (Ejaculatory Latency) | Non-Ejaculating Rats (% Ejaculating) |
|---|---|---|
| Percent Change | −15.2 ± 7.1 N = 9 | |
| Control | 772.1 ± 85.8 | 0.0 (0/10) |
| 100.0 mcg/kg | 415.1 ± 57.9* | 60.0 (6/10) |
| Percent Change | 43.9 ± 9.4 N = 12 | |

Asterisk denotes statistically significant changes
Control values were obtained from the same rats 2 weeks earlier following vehicle administration
All injections were made 30 minutes prior to testing
Values for Ejaculatory Latency are given in seconds The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 1 to about 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
|---|---|
| (+)-4-(Di-n-propylamino)-<br>1,3,4,5-tetrahydrobenz[c,d]-<br>indole-6-carboxylic acid,<br>methyl ester | 25 |
| Starch, dried | 425 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| (±)-4-(Di-n-propylamino)-<br>1,3,4,5-tetrahydro-benz[c,d]-<br>indole-6-carboxylic acid,<br>ethyl ester | 25 |
| Cellulose, microcrystalline | 625 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
|---|---|
| (±)-4-(Dimethylamino)-1,3,4,-<br>5-tetrahydrobenz[c,d]indole-6-<br>carboxaldehyde | 0.25 |
| Ethanol | 29.75 |
| Propellant 22 | 70.00 |
| (Chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made up as follows:

|  |  |
|---|---|
| (±)-4-(Di-n-propylamino)-<br>1,3,4,5-tetrahydrobenz[c,d]-<br>indole-6-carboxylic acid,<br>methyl ester | 60 mg |
| Starch | 45 mg |
| Microcrystalline cellulose | 35 mg |
| Polyvinylpyrrolidone<br>(as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

|  |  |
|---|---|
| (+)-4-(n-Propylamino)-<br>1,3,4,5-tetrahydrobenz[c,d]-<br>indole-6-carboxylic acid,<br>ethyl ester | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities. Such oral formulation is well suited for patients receiving treatment from depression.

Formulation 6

Suppositories each containing 225 mg of active ingredient may be made as follows:

|  |  |
|---|---|
| (±)-4-(Methylethylamino)-1,-<br>3,4,5-tetrahydrobenz-<br>[c,d]indole-6-carboxylic<br>acid, n-propyl ester<br>hydrochloride | 25 mg |
| Saturated fatty acid<br>glycerides | 2,000 mg |
| Total | 2,025 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| (+)-4-(Di-n-propylamino)-1,3,4,5-tetrahydrobenz[c,d]indole-6-carboxylic acid, methyl ester succinate | 5 mg |
| Sodium carboxymethyl cellulose | 95 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| (−)-4-(Di-n-propylamino)-1,3,-4,5-tetrahydrobenz[c,d]indole-6-carboxylic acid, methyl ester | 10 mg |
| isotonic saline | 1000 ml |

The solution of the above ingredients is administered intravenously at a rate of 1 ml per minute to a subject suffering from depression.

We claim:

1. A method for selectively blocking 5-$HT_{1A}$ receptors in a mammal said method comprising administering to said mammal an amount of a compound of the Formula I

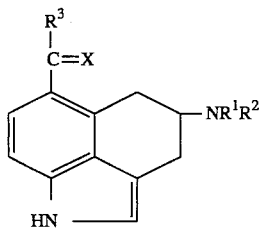

(I)

wherein:

$R^1$ is hydrogen, $C_1$–$C_4$ alkyl, allyl or

$R^2$ is hydrogen, $C_1$–$C_4$ alkyl or allyl;

$R^3$ is hydrogen, $C_1$–$C_4$ alkoxy, —$NR^5R^6$ or $C_1$–$C_4$ alkylthio;

$R^4$ is hydrogen, methyl, ethyl or vinyl;

$R^5$ and $R^6$ are independently a $C_2$–$C_4$ alkyl, a $C_1$–$C_4$ alkyl substituted with a phenyl group, or a phenyl group or $R^5$ and $R^6$ together form a $C_3$–$C_5$ heterocyclic ring;

X is O or S; or a pharmaceutically acceptable salt thereof, sufficient to block at least a portion of said 5-$HT_{1A}$ receptors.

2. A method of claim 1 which employs a compound of the Formula I wherein $R_5$ and $R_6$ are independently $C_1$–$C_4$ alkyl substituted with a phenyl group or a phenyl group or $R^5$ and $R^6$ together form a $C_3$–$C_5$ heterocyclic ring.

3. A method for enhancing the serotonin function in a mammal said method comprising administering to said mammal an effective amount of a compound of the Formula I

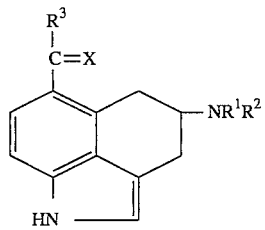

(I)

wherein:

$R^1$ is hydrogen, $C_1$–$C_4$ alkyl, allyl or

$R^2$ is hydrogen, $C_1$–$C_4$ alkyl or allyl;

$R^3$ is hydrogen, $C_1$–$C_4$ alkoxy, —$NR^5R^6$ or $C_1$–$C_4$ alkylthio;

$R^4$ is hydrogen, methyl, ethyl or vinyl;

$R^5$ and $R^6$ are independently a $C_2$–$C_4$ alkyl, a $C_1$–$C_4$ alkyl substituted with a phenyl group, or a phenyl group or $R^5$ and $R^6$ together form a $C_3$–$C_5$ heterocyclic ring;

X is O or S; or a pharmaceutically acceptable salt thereof.

4. A method of claim 3 which employs a compound of the Formula I wherein $R^5$ and $R^6$ are independently $C_1$–$C_4$ alkyl substituted with a phenyl group or a phenyl group or $R^5$ and $R^6$ together form a $C_3$–$C_5$ heterocyclic ring.

5. A method of treating anxiety or depression in mammals comprising administering to a mammal who is in need of treatment for any of such diseases, a pharmaceutically effective amount of a compound of the Formula I

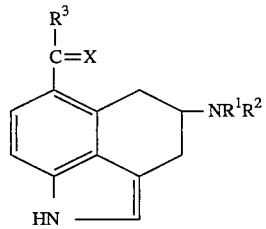

(I)

wherein:

$R^1$ is hydrogen, $C_1$–$C_4$ alkyl, allyl or

$R^2$ is hydrogen, $C_1$–$C_4$ alkyl or allyl;

$R^3$ is hydrogen, $C_1$–$C_4$ alkoxy, —$NR^5R^6$ or $C_1$–$C_4$ alkylthio;

$R^4$ is hydrogen, methyl, ethyl or vinyl;

$R^5$ and $R^6$ are independently a $C_2$–$C_4$ alkyl, a $C_1$–$C_4$ alkyl substituted with a phenyl group, or a phenyl group or $R^5$ and $R^6$ together form a $C_3$–$C_5$ heterocyclic ring;

X is O or S; or a pharmaceutically acceptable salt thereof, sufficient to block at least a portion of said 5-HT$_{1A}$ receptors.

6. A method of claim 5 which employs a compound of the Formula I where $R^5$ and $R^6$ are independently a phenyl group, $C_1$–$C_4$ alkyl substituted with a phenyl group or $R^5$ and $R^6$ together form a $C_3$–$C_5$ heterocyclic ring.

7. A method of treating anxiety or depression in humans comprising administering to a human who is in need of treatment for any of such diseases, a pharmaceutically effective amount of a compound of the Formula I

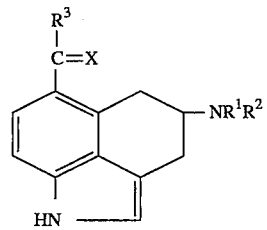

(I)

wherein:

$R^1$ is hydrogen, $C_1$–$C_4$ alkyl, allyl or

$R^2$ is hydrogen, $C_1$–$C_4$ alkyl or allyl;

$R^3$ is hydrogen, $C_1$–$C_4$ alkoxy, —$NR^5R^6$ or $C_1$–$C_4$ alkylthio;

$R^4$ is hydrogen, methyl, ethyl or vinyl;

$R^5$ and $R^6$ are independently a $C_2$–$C_4$ alkyl, a $C_1$–$C_4$ alkyl substituted with a phenyl group, or a phenyl group or $R^5$ and $R^6$ together form a $C_3$–$C_5$ heterocyclic ring;

X is O or S; or a pharmaceutically acceptable salt thereof, sufficient to block at least a portion of said 5-HT$_{1A}$ receptors.

8. A method of claim 7 which employs a compound of the Formula I where $R^5$ and $R^6$ are independently $C_1$–$C_4$ alkyl substituted with a phenyl group or a phenyl group or $R^5$ and $R^6$ together form a $C_3$–$C_5$ heterocyclic ring.

* * * * *